(12) United States Patent
Foster

(10) Patent No.: US 6,893,450 B2
(45) Date of Patent: May 17, 2005

(54) MINIMALLY-INVASIVE MEDICAL RETRIEVAL DEVICE

(75) Inventor: Thomas L. Foster, Poland, IN (US)

(73) Assignee: Cook Urological Incorporated, Spencer, IN (US)

( * ) Notice: Subject to any disclaimer, the term of this patent is extended or adjusted under 35 U.S.C. 154(b) by 202 days.

(21) Appl. No.: 09/954,234

(22) Filed: Sep. 14, 2001

(65) Prior Publication Data

US 2002/0068954 A1 Jun. 6, 2002

Related U.S. Application Data

(63) Continuation-in-part of application No. 09/277,098, filed on Mar. 26, 1999, now Pat. No. 6,500,182.
(60) Provisional application No. 60/232,523, filed on Sep. 14, 2000.

(51) Int. Cl.[7] .............................................. A61M 29/00
(52) U.S. Cl. ...................................................... 606/200
(58) Field of Search ................................ 606/110, 113, 606/114, 127, 200, 128

(56) References Cited

U.S. PATENT DOCUMENTS

| | | |
|---|---|---|
| 2,556,783 A | 6/1951 | Wallace |
| 4,046,150 A | 9/1977 | Schwartz et al. |
| 4,347,846 A | 9/1982 | Dormia |
| 4,393,872 A | 7/1983 | Reznik et al. |
| 4,607,620 A | 8/1986 | Storz |
| 4,611,594 A | 9/1986 | Grayhack et al. |
| 4,625,726 A | 12/1986 | Duthoy |
| 4,807,626 A | 2/1989 | McGirr |
| 5,030,201 A | 7/1991 | Palestrant |
| 5,197,968 A | 3/1993 | Clement |
| 5,376,094 A | 12/1994 | Kline |
| 5,376,100 A | 12/1994 | Lefebvre |
| 5,397,320 A | 3/1995 | Essig et al. |
| 6,174,318 B1 | 1/2001 | Bates et al. |
| 6,344,049 B1 * | 2/2002 | Levinson et al. ............ 606/200 |
| 6,368,338 B1 * | 4/2002 | Konya et al. ................ 606/200 |
| 6,500,182 B2 * | 12/2002 | Foster ......................... 606/127 |
| 6,511,492 B1 * | 1/2003 | Rosenbluth et al. ......... 606/159 |
| 2001/0031981 A1 * | 10/2001 | Evans et al. ................. 606/200 |
| 2002/0177872 A1 * | 11/2002 | Papp et al. .................. 606/200 |
| 2003/0135233 A1 * | 7/2003 | Bates et al. .................. 606/200 |

FOREIGN PATENT DOCUMENTS

| | | |
|---|---|---|
| DE | 197 22 429 A1 | 12/1998 |
| DE | 19839278 | 3/1999 |
| EP | 0 512 729 A1 | 11/1992 |
| EP | 0 512 729 B1 | 7/1995 |
| EP | 0 743 046 A1 | 11/1996 |
| EP | 0 818 180 A2 | 1/1998 |
| EP | 0 818 180 A3 | 5/1999 |
| EP | 0 818 180 B1 | 5/2003 |
| WO | 9505129 | 2/1995 |
| WO | WO 97/35522 | 10/1997 |
| WO | WO 97/39674 | 10/1997 |
| WO | 9948429 | 9/1999 |
| WO | 9956801 | 11/1999 |

* cited by examiner

Primary Examiner—Eduardo C. Robert
(74) Attorney, Agent, or Firm—Brinks Hofer Gilson & Lione

(57) ABSTRACT

A medical retrieval device is provided which includes an elongated cylindrical member having a passage extending therein and having a metallic proximal and distal portions. The proximal and distal portions are formed as separate pieces and connected at a junction. The elongated cylindrical member has an area of substantially constant inner and outer diameters extending at least from a portion of the proximal portion closely adjacent to the junction through the junction and to a portion of the distal portion closely adjacent to the junction.

11 Claims, 7 Drawing Sheets

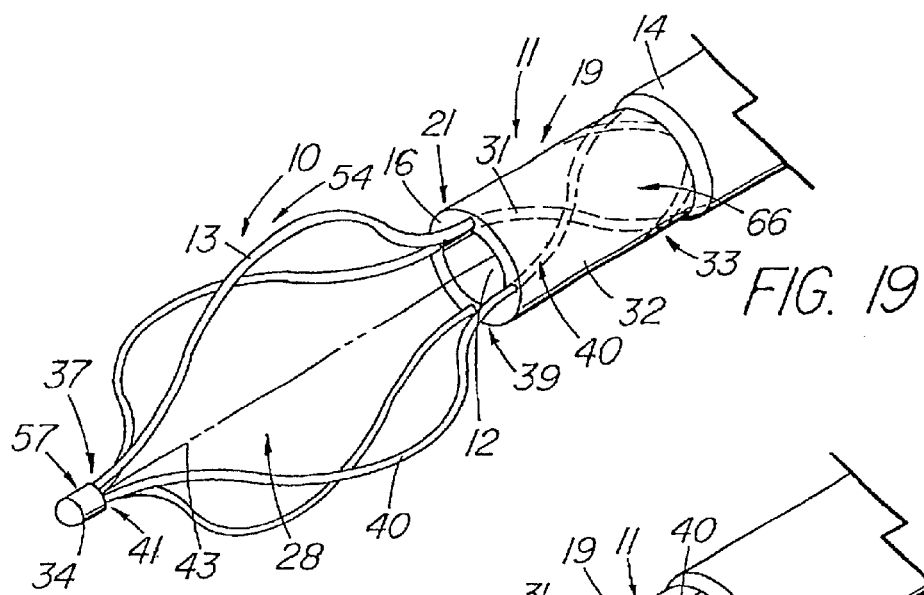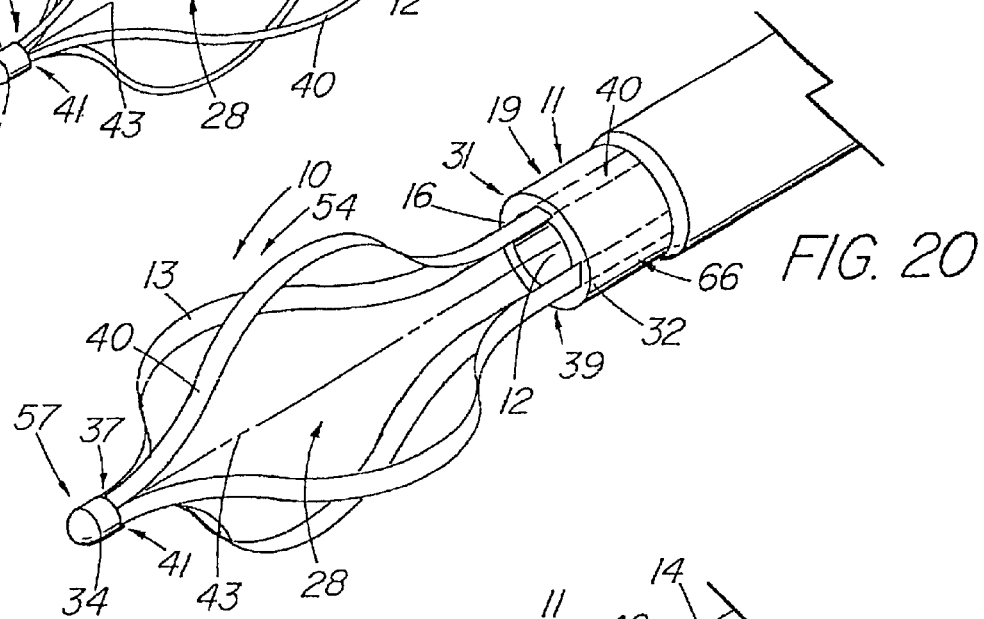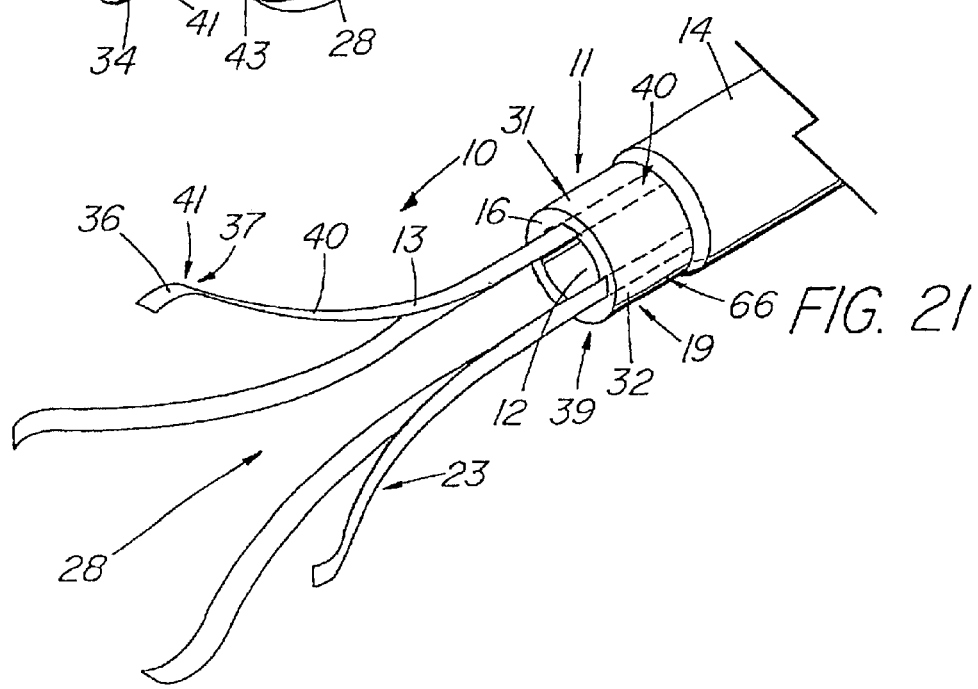

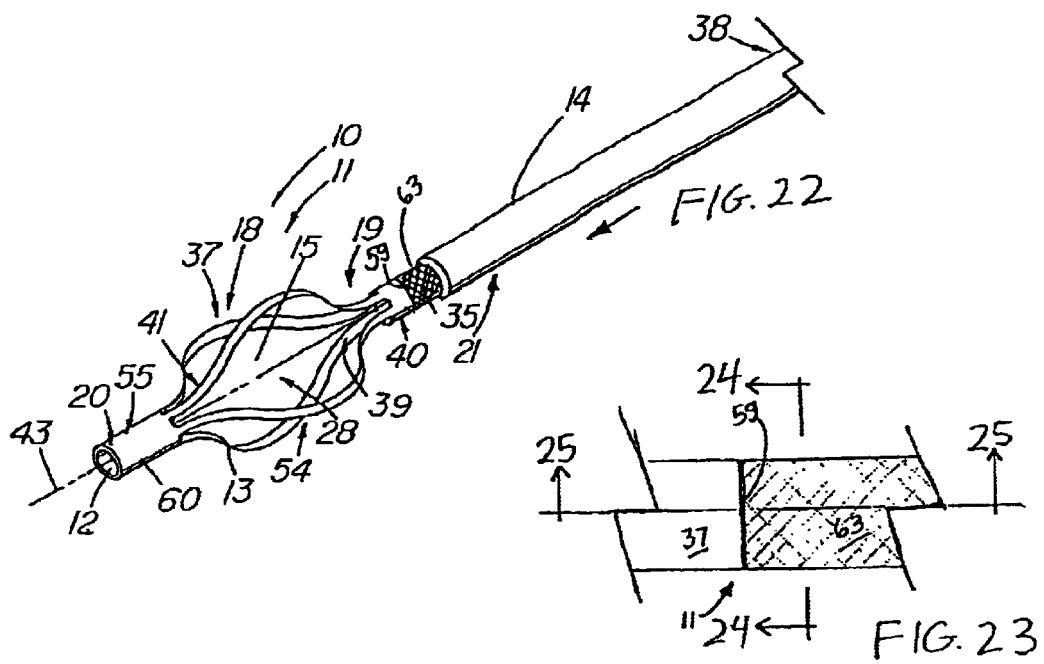
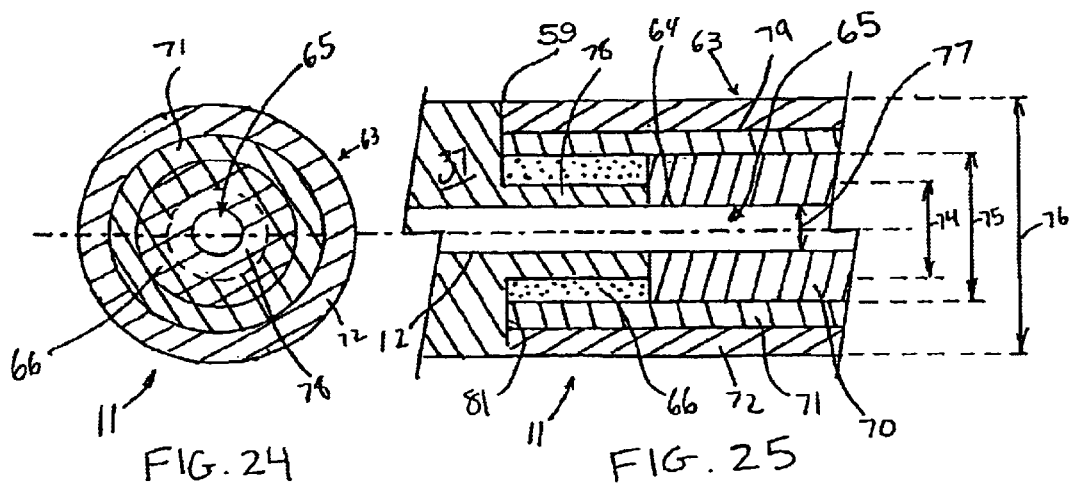

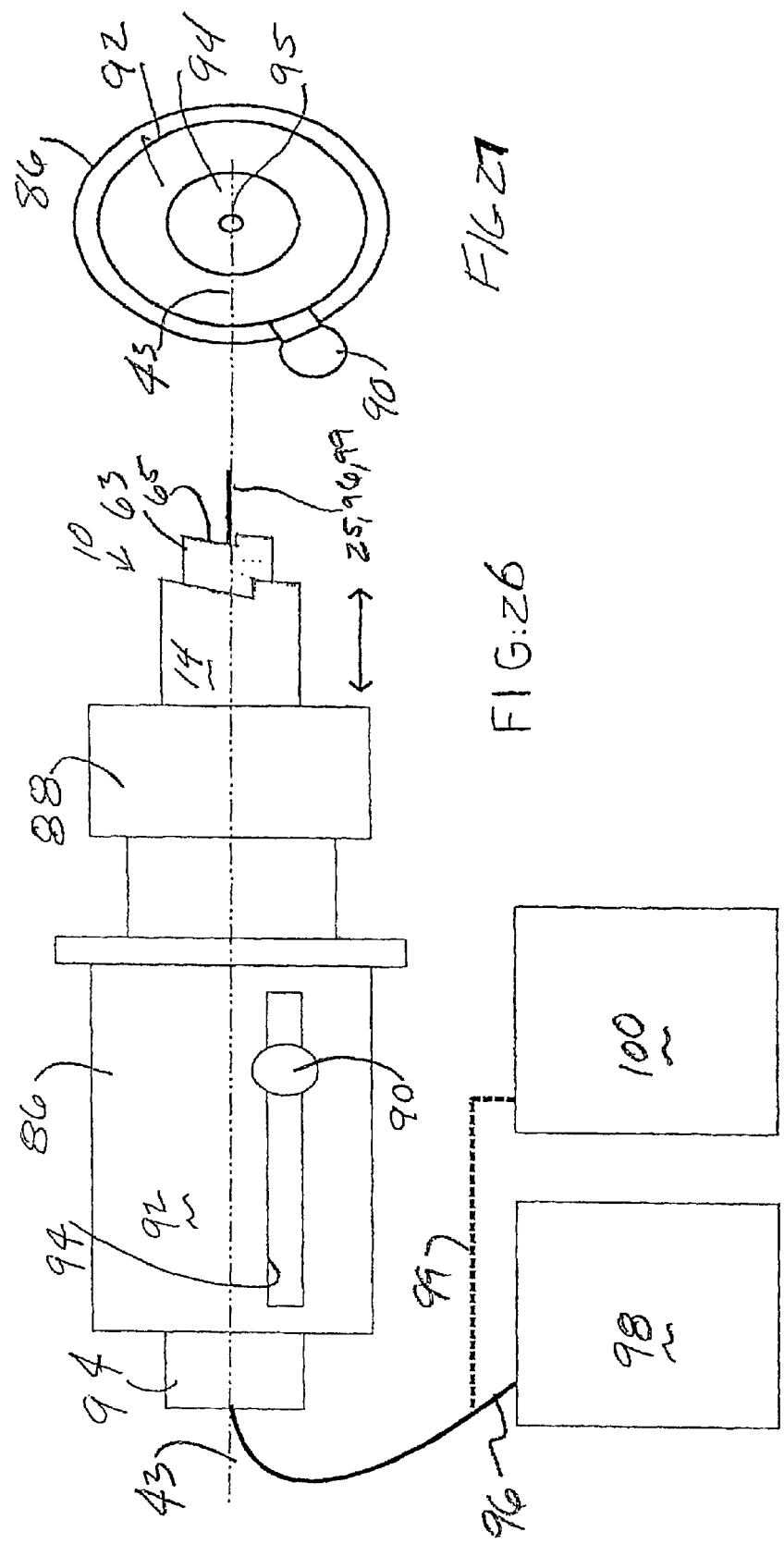

MINIMALLY-INVASIVE MEDICAL RETRIEVAL DEVICE

CROSS-REFERENCE TO RELATED APPLICATIONS

This application claims priority of U.S. provisional application Ser. No. 60/232,523 filed Sep. 14, 2000 and is a Continuation-in-Part of U.S. patent application Ser. No. 09/277,098 filed Mar. 26, 1999, now Pat. No. 6,500,182.

TECHNICAL FIELD

This invention relates generally to medical devices, and in particular, to medical retrieval devices for engaging and/or removing objects, such as calculi and the like, from the body.

BACKGROUND OF THE INVENTION

Various organs and passages in the body are subject to the development of stones, calculi and the like. Gallstones are a common problem at least in the United States and are the most frequent cause of gallbladder inflammation. Calculi in other parts of the biliary system are also commonplace. Similarly, stones, calculi and the like can develop throughout the renal or urinary system, not only in the ureters and distal to them, but also in the renal tubules and in the major and minor renal calyxes. The calyxes are hollow collecting structures in the kidneys, extending from the renal pelvis, the minor calyxes in particular joining the renal pyramids. For simplicity, the calyxes can be considered as ducts extending from the connecting tubules of the renal nephrons to the ureters.

Minimally invasive surgical procedures have been developed for the removal of stones, calculi and the like from the biliary and urinary systems. Such procedures avoid the performance of invasive, open surgical procedures (such as, for example, the cholecystectomy) and can instead employ percutaneous access, in which stones, calculi and the like are removed through a percutaneously inserted access sheath. Several access routes are suitable, depending upon the specific system and the particular location in the system at which the stones, calculi or the like are found. Without regard to the access route, however, percutaneous removal is usually based upon the use of either forceps or basket-tipped catheters to engage and remove the stones, calculi, and the like.

A closed, wire-tipped basket (helical or straight wire) permits entry of the stone or the like from the side of the basket, while an open ended basket allows a head-on approach to the stone or the like. Other retrievers and graspers can include forceps or can include a loop or snare for encircling the body to be removed, the loop or snare being made of, for example, round or flat wire. Flat wire has the advantage over round wire in that baskets incorporating flat wire exhibit better resistance to twisting during use. Moreover, while surgical techniques have advanced, and endoscope accessory channels of a relatively smaller diameter have been developed, efforts to reduce the diameter of round wires incorporated in stone extraction baskets have unfortunately not met with similar success. In practice, the lowest useful round wire diameter remains about 0.007 to 0.010 in. (about 0.178 to 0.254 mm). Because there is a significant amount of wasted space inside any sheath or cannula containing round or flat wires, this limit on useful wire diameter has prevented the development of useful stone extractors of small diameter, and in particular, of extractors having an outside diameter (that is, the diameter of the sheath or cannula containing the wires) below about 1.7 French (0.022 in. or 0.56 mm).

Another desirable feature of smaller retrieval devices, especially important for urological use, would be to have a device that works with a small diameter endoscope, such as an ureteroscope, that is capable of accommodating accessory instrumentation such as a laser fiber or hydraulic lithotripsy wire to break up stones or calculi for easier removal. The limited space and limited number of lumens available in the smaller scopes makes it advantageous to create devices that are capable of sharing the existing accessory channels of the endoscope without having to increase the diameter of the lumen(s) within the scope. While some small-diameter retrieval devices are capable of being introduced through a ureteroscope, the size and design of the wire precludes having an internal lumen through which accessory instrumentation, such as that for performing a lithotripsy procedure, can be introduced into the workspace of the retrieval device.

SUMMARY OF THE INVENTION

The foregoing problems are solved and a technical advance is achieved in an illustrative medical retrieval device which is particularly useful with an endoscope for engaging or capturing, breaking up and removing, extracting, or retrieving objects such as stones, calculi, concretions, foreign bodies and the like from a variety of locations in the body. The disclosed embodiments of the present medical retrieval device can each be characterized as including an elongated member wherein the resilient grasping members of the distal portion of the elongated member represents a continuum of a material that includes at least a portion of the elongated member. A proximal portion of the elongated member may be constructed of the same or a different material than the continuum comprising the grasping members and the distal portion of the elongated member. The resilient members form either a basket or a forceps.

In one embodiment of the present invention, the individual grasping members result from longitudinally slotting or slitting the distal portion of the elongated member about one end. The distal portion of the elongated member can be a hollow cannula or a solid member, preferably cylindrical in shape. The slots are formed by removing material from the distal portion of the elongated member in the form of longitudinal, elongated slots. The resilient grasping members result about the circumference of the elongated member with the remaining material thereof. Alternatively, the members result from the removal of material to expose elements, such as reinforcement wires, that are already encased within the walls of the elongated member. Advantageously, the members can comprise a basket or snare when the grasping members are interconnected at the distal end of the device, or grasping forceps when they are not.

Basket-making methodology has previously involved soldering, welding, crimping, or otherwise attaching the basket wires to a separate shaft piece. By having the wires or resilient grasping members being continuous with the distal portion of the elongated member, a joint at the ends of the basket wires is advantageously eliminated. Such a joint can be more subject to breakage, possibly resulting in the dangerous situation of having a loose broken wire within the patient. Another advantage of a retrieval basket, grasper, or forceps of the present invention made from a thin-walled cannula or tube is the large open lumen and a small relative O.D. This large open lumen advantageously permits lithotripsy procedures to be performed when the retrieval device is inserted through a ureteroscope. The present invention is particularly advantageous over the prior art in that the device can have an overall outside diameter significantly smaller than the outside diameter of existing retrieval or extraction devices, wherein the joint between wires and shaft increases the outer diameter and/or the available inner lumen diameter. The retrieval device of the present invention can have an outside diameter as small as 1 French (0.33 mm), although 2–3 French (0.667–1.0 mm) is a preferred size for use in conjunction with a ureteroscope and laser fiber or lithotripsy laser fiber. Smaller devices will be able to reach deeper inside the body to capture and retrieve stones and calculi. It should go without saying that the smaller diameter is also expected to reduce the risk of patient discomfort and the risk of inadvertent damage to tissue during introduction and manipulation of the device in the patient.

Visualization of the target object is essential when using a retrieval device. Endoscopes, used in most minimally invasive procedures to retrieve stones or calculi, typically have a second or third accessory channel or lumen for introducing ancillary devices to the treatment site. The smaller diameter endoscopes, such as a ureteroscope, have a very narrow accessory channel through which the retrieval device is fed. An advantage of the present invention is that the tubular design, with its large central lumen, allows the introduction of additional instrumentation useful to the procedure such as a guidewire that may be used for placement, or a device to break up a stone or calculus such as a laser fiber or electrohydraulic lithotripsy wire. Conventional basket or grasper forceps manufacturing techniques that require soldering basket wires to the device shaft and/or compacting the basket wires into a narrow diameter, do not leave sufficient additional room for other devices within the narrow working channel. While the central lumen is useful for introducing instruments into the inner working area, alternative embodiments include filling the end of the cannula with solder or another material to form a tip that is less traumatic to tissue.

An additional advantage of the present invention is the relative simplicity of construction. Devices comprised of a metal cannula or cylinder can be formed by making a series of longitudinal slots or slits through the cannula/cylinder to form individual resilient grasping members. The process results in perfectly aligned grasping members and, except for reforming the grasping members, eliminates much of the skilled hand work normally required to assemble a basket or grasper forceps. Plastic deformation or heat setting the resilient grasping members into the outwardly extending configuration of a basket or forceps advantageously removes bending stresses and puts the expanded device in a relaxed condition during deployment. Retrieval devices of the present invention can use an external constraining mechanism such as a coaxial outer sheath or endoscope to open and close the resilient grasping members which capture and retain the target object for removal from a patient. Alternative methods could include an actuating member disposed in the lumen of the device to open and close the basket or grasper forceps, or forming only one slot or slit into the side wall at the distal end portion.

In another embodiment of the present invention, the retrieval device is formed from an elongated member comprising a plastic tube having reinforcement wire encased therein. These wires, each representing a continuum of material extending the length of the distal portion of the elongated member, are exposed within the distal portion of the tube that interconnects them, where they are then formed into the resilient grasping members for making a retrieval basket or grasping forceps.

Factors affecting the ability of an operator to percutaneously engage and/or remove stones, calculi, and the like include the strength of the grasper portion of the equipment to retain and remove the stones, and the capacity to break larger stones for removal while protecting the equipment from the energy used to break the stones. In addition, the use of a laser or other lithotripsy device has conventionally required a large central lumen through which a clad fiberoptic cable is passed to address the stone. A basket or grasper made of a metal such as stainless steel of the 300 or 400 series or a nickel-titanium alloy such as nitinol and having a metal shaft extending back to the proximal end defining the central lumen, provides strength to handle and remove stones from a patient's body. The metal structure extending from the proximal end of the device to the distal end of the grasper or basket and surrounding the central lumen, protects the endoscope and surrounding tissue from laser energy which may be misdirected due to a defect in the laser fiber. A defect such as a nick in the fiber could direct the laser energy into the side wall of the endoscope, damaging the instrument and destroying its functionality. The use of a metal structure for the distal portion of the elongated member and a lightweight, flexible material such as a coated wire braid comprising the proximal portion, or shaft, overcomes these challenges to removing stones and calculi from a patient's body.

Where a second material is used for the proximal portion of the elongated member, or shaft of the retrieval device, the second material may be selected for its flexibility, cost and strength. The shaft made of the second material is attached to the distal portion of the elongated member comprising the grasping members to form a multi-part retrieval device. Retrieval devices of the present invention can use an external constraining mechanism such as a coaxial outer sheath or endoscope to open and close the resilient grasping members which capture and retain the target object for removal from a patient. Alternative methods could include an actuating member disposed in the lumen of the device to open and close the basket or grasper forceps.

In one embodiment of the present invention, the retrieval device is formed from two pieces, each piece, the proximal portion (or shaft) and the distal portion of the elongated member, having a passage extending from end to end. The pieces are attached to form the device having their respective passages concentric to each other thereby forming a central, continuous lumen through the entire retrieval device from the proximal end of the shaft to the area proximate to the basket, grasper or forceps. This central lumen is used to extend a fiber optic wire or lithotripsy wire from a power supply, controlled by an operator outside the patient, to a position proximate to an object in the grasp of the basket, grasper or forceps.

BRIEF DESCRIPTION OF THE DRAWINGS

Embodiments of the invention will now be described by way of example with reference to the accompanying drawings, in which:

FIGS. 19–21 depict pictorial views of further embodiments of the present invention in which the resilient grasping members of the device include strips or wires of one material that have been exposed from within the walls of a tube of another material;

FIG. 22 is a pictorial view of a still further embodiment of the present invention in which the device of FIG. 1 is shown having a junction between a distal portion and a proximal portion, or shaft, of the elongated member;

FIG. 23 is an enlarged fragmented elevational view of the device of FIG. 22 showing the junction between the distal portion and the shaft;

FIG. 24 is a cross-sectional view of the device of FIG. 22 taken along line 24—24 of FIG. 23;

FIG. 25 is a longitudinal sectional view of the device of FIG. 22 taken along line 25—25 of FIG. 23;

FIG. 26 is a pictorial view of the device of FIGS. 1 to 25 used with a handle and either a laser device or a lithotripsy device; and FIG. 27 is an end view of the handle of FIG. 26.

DETAILED DESCRIPTION

Figure 1:
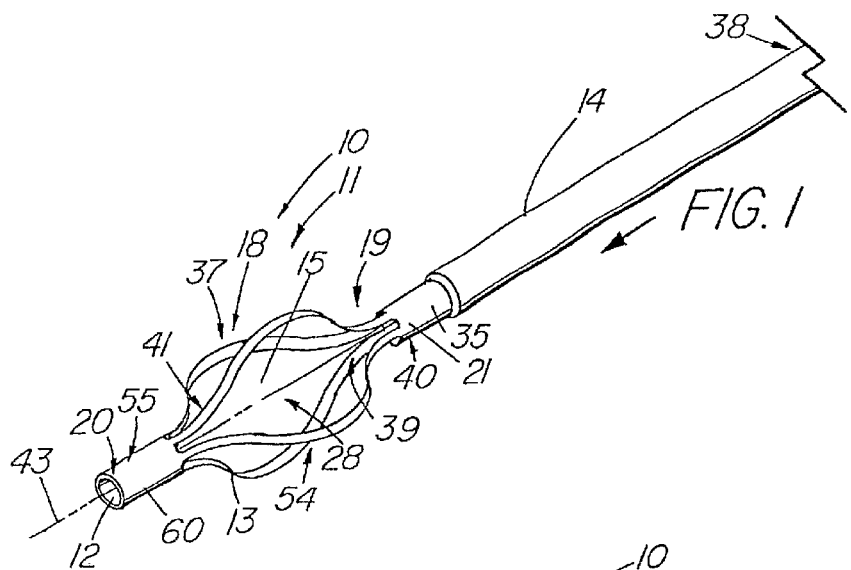
FIG. 1 depicts a pictorial view of a medical retrieval device of the present invention.

The medical retrieval device 10 of the present invention, as shown in FIG. 1, comprises an elongated member 11 that includes a distal portion 37 and a proximal portion 21. The distal portion 37 includes a plurality of resilient grasping members 13 that are formed to provide a workspace volume 28 that provides the working space to capture and manipulate objects. The distal portion 37 of the elongated cylindrical member 11 includes a continuum of a first material 40 such as stainless steel or nickel-titanium alloy which is a single continuous element, rather than being comprised of two or more distinguishable or connected elements of a single material (or different materials) that are soldered, crimped, or conjoined in some other manner.

In the embodiments depicted in FIGS. 1–18, the continuum of first material comprises a single cannula 60 or a solid rod 62 from which medical retrieval device 10, such as a basket 54, grasping forceps 23, or snare 26, is formed. While it is preferable that a round or otherwise cylindrical cannula or rod is used, the elongated member 11 could have polygonal or other noncircular cross-section. The continuum of first material 40 preferably is comprised of a suitable resilient material for forming the resilient grasping members. Any elastic material that can retain bending stresses and resiliently return to its preformed shape may be used. Metal is the preferred material for making a medical retrieval device 10 with the most preferred materials being stainless steel or an alloy having superelastic properties such as an alloy of nickel-titanium commercially available as nitinol (NiTi). The preferred stainless steel would be one in the 300 series with the 400 series also providing an alternative material. Certain polymer materials having a sufficient modulus of elasticity can also be used in larger sized devices. Superelastic materials like nitinol are preferred for the smallest devices (less than 4 Fr. (1.33 mm)) with very thin wall thicknesses because of their improved resistance to fracture or kinking.

The preferred method of forming the resilient grasping members 13 from the distal portion 37 of the elongated member is to remove material of the elongated member 11 by creating slots 15, or slits, or open areas or spaces between the resilient grasping members 13. In the illustrative embodiment, four resilient grasping members 13 are formed from cannula 60 by the establishment of slots 15 through the walls 16 of distal portion 37 of the elongated member 11, in particular the cannula 60.

Figure 2:
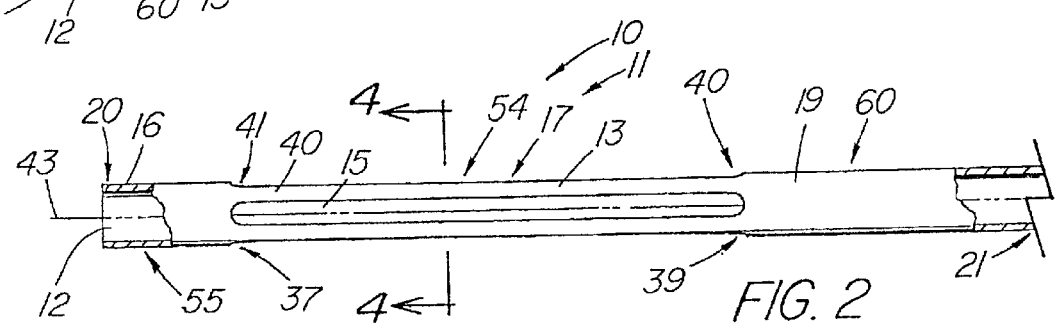
FIG. 2 depicts a side view of the device of FIG. 1 in an unexpanded or compact state.
Figure 4:
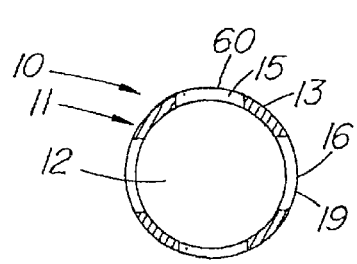
FIG. 4 depicts a cross-sectional view of the device of FIG. 2 taken along line 4—4 thereof.

FIG. 2 depicts a side view of the cannula 60, showing the distal portion 37 of the elongated member 11 prior to reshaping of the resilient grasping members. FIG. 4 depicts a cross-sectional view of the device of FIG. 2 taken along line 4—4. Slots 15, equal in number to the desired resilient grasping members, are incorporated into the wall 16 of the elongated member. When a hollow metal cannula 60 is used such as in the embodiment depicted, the unwanted material between the resilient grasping members 13 can be removed by a cutting means such as a standard EDM wire machine or a laser. Alternative methods include water jet, machining, or chemical etching. When an EDM wire machine is used, a pilot hole for the continuous EDM wire is drilled through the elongated member 11. The diameter of the cutting wire or laser determines the width of the slots 15 and consequently, the width, thickness, and/or diameter of the resilient grasping members 13. An alternative method of cutting the slots into a cannula would be to insert a rod and then set a laser (or other cutting instrument with similar capabilities) to make a cut of predetermined depth which is prevented from extending through the opposite side of the cannula 60 by the inserted rod. Still another method would be to create the slots, spaces, or openings during initial fabrication of the elongated member 11, especially in the case of a device made of plastic. In the illustrative embodiment, the slots 15 terminate prior to the distal end 20 of the elongated member 11, leaving a distal closed cylinder 55 like the proximal closed cylinder 19 that comprises the proximal end of the distal portion 37 at the termination of the ends of the proximal ends of the grasping members 13. The distal closed cylinder 55 provides the means to unite the distal ends 41 of the resilient grasping members, eliminating the need for a separate connection such as solder joint or a crimping device.

Figure 17:
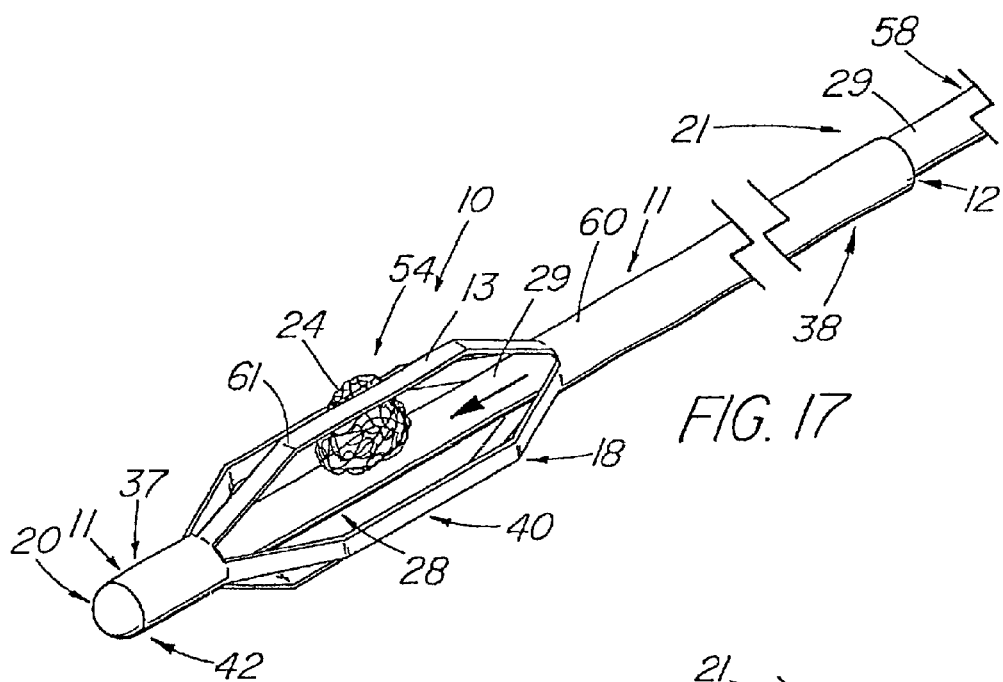
FIG. 17 depicts a pictorial view of still yet another alternative embodiment of the present invention in which the device includes an actuating member.

After the longitudinal slots 15 are initially formed, the resilient grasping members 13 have a compact shape 17 in which they are essentially parallel with the longitudinal axis 43 of the elongated member. In the cannula 60 embodiments, this produces an elongated member 11 with its original and maximal lumen size and essentially no increase in overall diameter of the retrieval device 10 while it is in the compact or compressed shape 17, as depicted in FIG. 4. Returning to FIG. 1, a basket 54 is formed by plastically deforming the individual resilient grasping 13 members into a second, outwardly projecting, expanded shape 18 such that a workspace volume 28 is created between the outwardly projecting grasping members in which calculi can be ensnared for retrieval or manipulation. The grasping members can be given any shape that creates an open region for capturing objects such as the arcuate shape of FIG. 1, or an angular shape created by introducing bends 61 in the resilient grasping members 13 as shown in the embodiment of FIG. 17.

Referring still to FIG. 1, if the retrieval device 10 of the present invention is to be made of nitinol, instead of stainless steel, the slots 15 are cut and resilient grasping members 13 are formed into the enlarged shape 18 using a mandrel or fixture to retain the shape. The device is then heat set or "trained" into the enlarged shape 18, wherein the bending stresses of the resilient grasping members are removed. For example, the temperature for thermally setting the finished device may be 500° C. or higher. The transformation temperature, at which the material changes from the malleable martensitic state to the shape memory austenitic state must be below that at which the device is used so that the resilient grasping members retain their shape and have sufficient resiliency to function as a retrieval device. This temperature can be set below room temperature, e.g., 10° C., or it may be set at a point between room temperature and body temperature so that the device may be easily loaded into the outer sheath while in a martensitic state. An alternative method of forming bends in nitinol is plastically deforming the material in a manner known as cold working as disclosed in PCT application publication No. WO 00/33909. The nitinol is mechanically overstressed such that there is a localized phase change that results in a permanent bend at that site.

To effect opening and closing of the retrieval basket 54, an external restraining mechanism 14 such as a coaxial outer sheath is used as shown in FIG. 1. When it is important to minimize the overall size of the device, it is naturally important to select the smallest sheath 14 that permits axial movement over the elongated cylindrical member 11. To reduce friction between the elongated cylindrical member 11 and the external constraining mechanism 14, it is advantageous to add a thin layer 35 of lubricious material such as polytetrafluoroethylene (PTFE) to the outer surface of the shaft 63 of the retrieval device 10.

Figure 12:
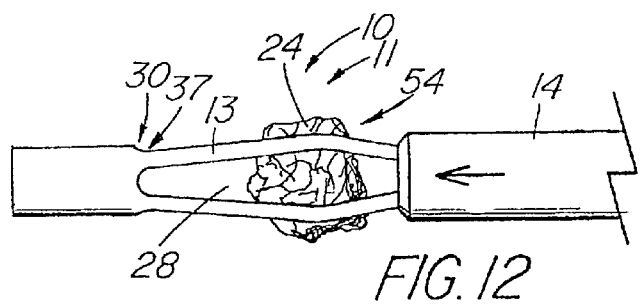
FIG. 12 depicts a side view of the device of FIG. 1 in a closed position with a captured calculus.

FIG. 12 depicts a side view of the device of FIG. 1 in the closed position 30 with a captured calculus 24. In the absence of a calculus 24 or other captured object, the substantially closed position 30 would be essentially the same as the compact position of FIG. 2. The external constraining mechanism 14 is advanced over the resilient grasping members 13, resiliently deforming and radially compressing the resilient grasping members 13 from their proximal ends 39 until the resilient grasping members 13 firmly secure the calculus within the constricted workspace volume 28. If desired, the retrieval device 10 and the retrieved object 24 can then be removed from the body together.

Figure 3:
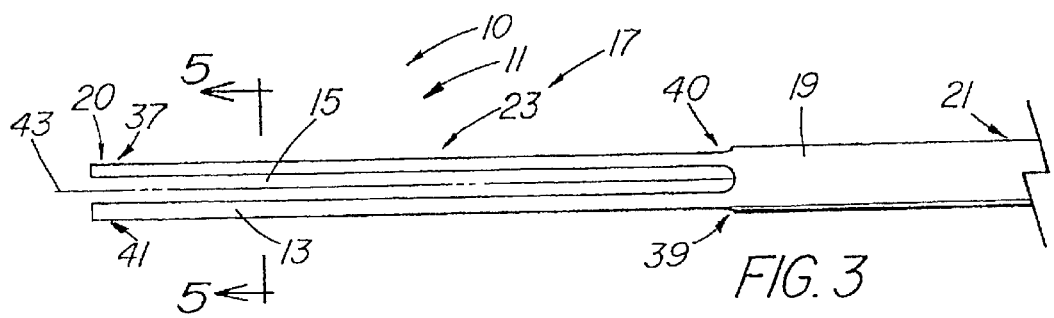
FIG. 3 depicts a side view of an alternative embodiment of the device of the present invention comprising a grasper forceps in an unexpanded state.
Figure 7:
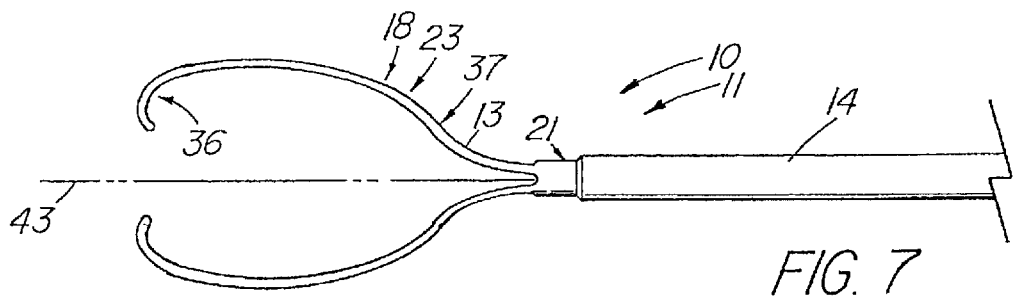
FIG. 7 depicts a side view of the device of FIG. 3 in an expanded state.

FIG. 3 depicts a side view of an alternative embodiment of retrieval device 10 of FIG. 1 that comprises a set of grasper forceps 23 with the resilient grasping members 13 in the compact shape 17. A grasper forceps is essentially manufactured the same as the device of FIG. 1 with the exception that the slots 15 extend to the distal end 20 of the elongated member 11. As with the manufacture of baskets, the resilient grasping members are plastically deformed or heat set to an open position 18, as depicted in FIG. 7, for receiving an object from within a patient. To facilitate capture and retention of the object, the distal tips 36 of the resilient grasping members may be bent inward. The resilient grasping members close upon the target object by means of the external constraining mechanism 14 which is advanced in the same manner as with the basket 54 of FIG. 1.

Figure 8:
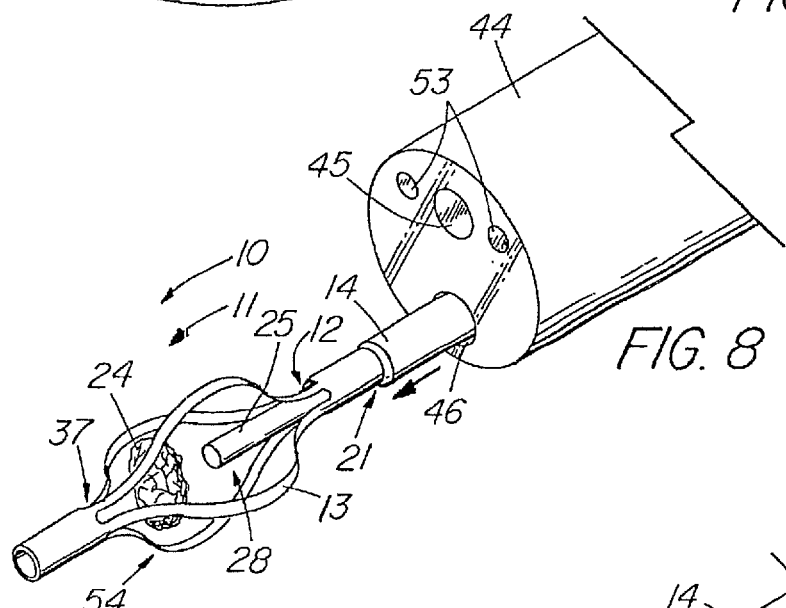
FIG. 8 depicts a pictorial view of the device of FIG. 1 being used with an endoscope to locate and break up a calculus.

FIG. 8 depicts a pictorial view of the retrieval device 10 of FIG. 1 showing how it may be used in combination with ureteroscope 44. For retrieval of calculi within the urinary tract, a standard ureteroscope 44 is typically used which includes an optical lens 45 connected to a series of lenses or optical fibers to permit visualization of the target, a light source 53 for illumination, and at least one accessory channel 46 for the introduction of instrumentation and/or the passage of fluids. The accessory channel 46 of a typical ureteroscope can range from 2.0 Fr (0.667 mm) up to at least 6 Fr (2 mm). The illustrative embodiment, which has an outer diameter of about 3 Fr (1 mm), can be used with a 3.4 Fr (1.133 mm) accessory channel. The outer diameter of the compressed basket 54 or elongated cylindrical member 11 is about 2.5 Fr (0.833 mm) with the passage 12 about 2 Fr (0.66 mm) in diameter. The passage or lumen 12 can accommodate a standard laser lithotripsy wire which is about 200 microns in diameter, excluding cladding. The laser delivers energy to the calculus 24, breaking it into smaller fragments that can be passed through the ureter or retrieved through the passage 12 of the device. While the use of a small size retrieval device 10 advantageously permits its passage through an endoscope, it is contemplated that larger basket or forceps embodiments of the present invention, such as 9 Fr (3 mm) or larger, can also be utilized for general retrieval applications in the body as well, especially where a large central lumen is desired.

Figure 6:
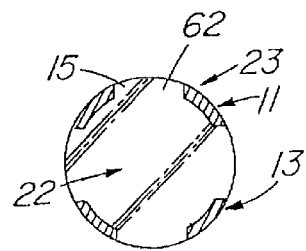
FIG. 6 depicts a cross-sectional view of an alternative embodiment of FIG. 3 taken along line 6—6 of FIG. 3 in which the alternative embodiment is formed from a solid member having a distal end bore.

A further benefit of forming retrieval device 10 from a cannula is the resulting arcuate cross-sectional shape of the resilient grasping members (as shown in FIGS. 4 and 6). Given an arcuate-cross-sectional-shaped resilient grasping member and a flat or bar cross-sectional-shaped member of an identical size and material, an individual arcuate-cross-sectional-shaped resilient grasping member is shown empirically to be able to exert about 25 percent more force inwardly against the target object. This demonstrated structural advantage is similar to that of an I-beam which is used as a girder design in building construction due to its superior strength.

Figure 5:
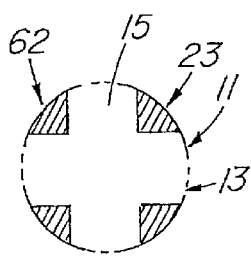
FIG. 5 depicts a cross-sectional view of an alternative embodiment the device of FIG. 3 taken along line 5—5 of FIG. 3, formed from a solid member and showing wedge-shaped resilient grasping members.

In addition to being made from a cannula, baskets and grasper forceps of the present invention can be fabricated from a solid elongated member. FIG. 5 depicts a cross-sectional view of elongated cylindrical member 11 taken along line 5—5 of FIG. 3 of an alternate embodiment thereof formed from a solid member and having wedge-shaped resilient grasping members. The wedge-shaped grasping members depicted can be formed by creating two slots through the elongated member in essentially the same manner as with the embodiments made from a metal cannula. Baskets and graspers made from wedge-shaped grasping members are advantageously compressed into a smaller diameter than those of standard round or flat wire and are further disclosed by Bagley et al. in a patent assigned to the present assignee entitled, "Minimally Invasive Retriever Including Wedge-Shaped Wires", having U.S. Pat. No. 6,203,552, which is incorporated herein by reference.

FIG. 6 depicts a cross-sectional view, looking proximally, of an alternative embodiment FIG. 3 in which the device has been formed from solid member 62, wherein the resilient grasping members 13 are essentially arcuate in shape. They are formed by creating a central bore 22 into the distal end 20 of the solid elongated member to a point at least near to where the proximal ends of the resilient grasping members will be. The slots 15 are then formed to produce a grasper forceps of the compact shape 17, which are then formed into an enlarged shape 18 in the same manner as the embodiment of FIG. 7. The arcuate-shaped grasping members of the embodiment of FIG. 6 are of the same general shape as if formed from a cannula, although the central bore will not normally extend substantially or at all beyond the proximal ends of the resilient grasping members. Generally, graspers and baskets made from solid cylindrical stock would have a solid shaft or proximal portion 21 without a central lumen and therefore, would not be able to accommodate an additional instrument or device.

Figure 9:
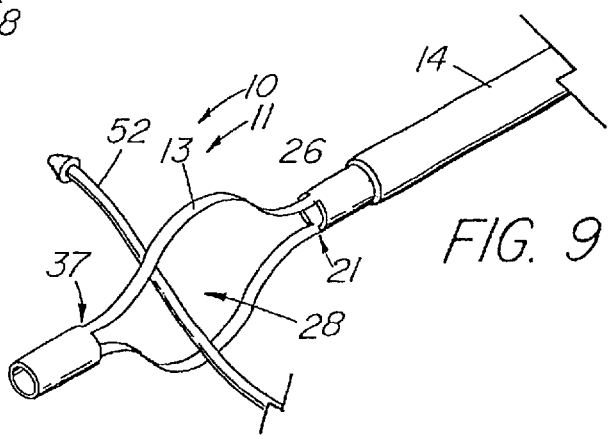
FIG. 9 depicts a pictorial view of an alternative embodiment of the device of the present invention comprising a snare.

The embodiments depicted in FIGS. 1–8 disclose retrieval devices having four resilient grasping members; however, devices having two to eight grasping members are feasible. FIG. 9 depicts a pictorial view of an alternate embodiment of retrieval device 10 of FIG. 1 having two resilient grasping members 13 formed by cutting a single slot. A retrieval device of this type can be especially useful as snare 26 for retrieving elongated foreign objects 52 such as catheters, pacemaker leads, etc.

Figure 13:
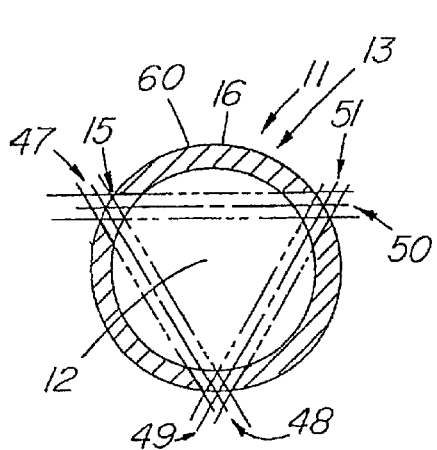
FIG. 13 depicts a cross-sectional view of an alternative embodiment of the present invention in which the device includes three resilient grasping members.

FIG. 13 depicts a cross-sectional view of an unexpanded alternate embodiment of the device of FIG. 1having three resilient grasping members 13 formed by three slots 15. In this particular embodiment, the pathways that form the three slots 47; 48,49; and 50,51 create an imaginary triangle in cross-section. In this discussion, "slots" refer to a single longitudinal opening through the cannula wall, while "pathway" refers to an imaginary line passing through two different slots on the cannula, indicative of how the slot is formed. Therefore, a single slot may have two different element number designations (e.g., 48,49 and 50,51). The first slot 47 is formed through the elongated cylindrical member such that the resulting exit slot 48 lies 120° along the circumference of the cylinder with respect to the first entrance slot 47, rather than diametrically opposed as with devices having an even number of grasping members. To create a third slot 50, a second entrance slot 49 is formed whereby either the entrance slot 49 or second exit slot 51 is the same as either the first entrance slot 47 or first exit slot 48 which are already formed. For example, a second pathway 49–51 can be precut through the first exit slot 48 for the EDM wire to create a second exit slot 51 120° from the second entrance slot 49/first exit slot 48, and 120° from the first entrance slot 47. An optional third entrance slot 50 can be made through the second exit slot, passing through the first entrance slot to finish the edges in a uniform manner; however, these two slots will have already been formed. This method is not limited to a device having three grasping members. For example, a device having five grasping members would require that the slots be formed at 72° intervals along the circumference of the cylinder with slot pathways forming an imaginary pentagon. An alternate method of forming an odd number of slots would be the technique described above in which a rod is inserted, and the slots are cut at the desired intervals, rather than two being formed with a single cut.

Figure 14:
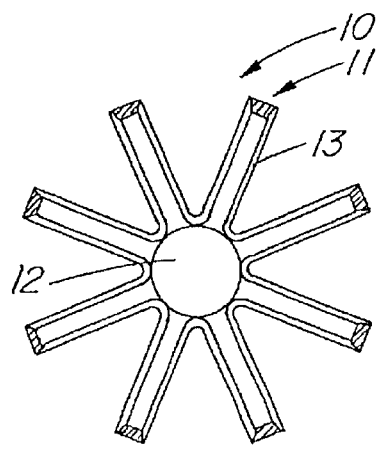
FIG. 14 depicts a cross-sectional view of another alternative embodiment of the present invention having eight resilient grasping members.

FIG. 14 depicts a cross-sectional view of an expanded alternate embodiment of retrieval device 10 of FIG. 1 having eight resilient grasping members 13. Such a basket would be advantageous for capturing and retaining smaller objects.

Figure 10:
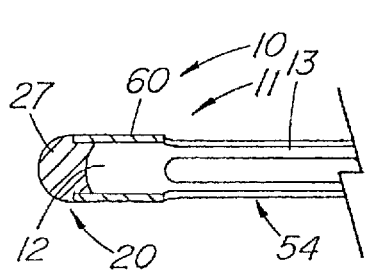
FIGS. 10–11 depict side views of alternative embodiments of the device of the present invention wherein the distal end of the device includes a solid tip.

FIG. 10 depicts a side view of an alternate embodiment of retrieval device 10 of FIG. 1 wherein the distal end 20 is soldered closed. The solder joint 27 within the tip is finished by grinding and/or polishing. The polished tip helps prevent trauma to delicate tissues during use of the device. Closing the distal end does not interfere with feeding a laser fiber or other device through the lumen to treat an ensnared calculus; however, an open distal end would be advantageous if the capability to feed the device over a guidewire is desired.

Figure 11:
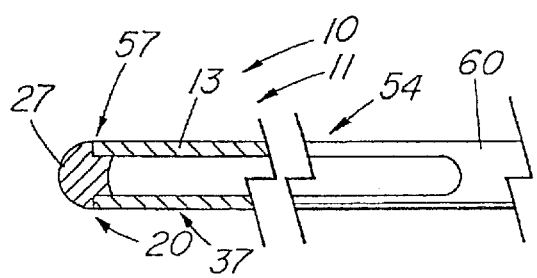

FIG. 11 depicts a side view of an alternate retrieval basket 54 of device 10 of FIG. 1, wherein rather than a distal cylinder 55 (intact portion of cannula 60) interconnecting the distal ends 41 of the resilient grasping members 13, a fastener 57 such as a solder joint 27 is used. As used herein, fastener 57 can comprise any well-known method of joining the resilient grasping members such as a cap, crimp, band, weld (including spot weld), or adhesive. This method of joining the resilient grasping members 13 provides an alternate method of creating a retrieval basket 69 whereby the elongated member 11 can be cut the same as the grasping forceps 23 embodiments depicted in FIG. 3.

Figure 15:
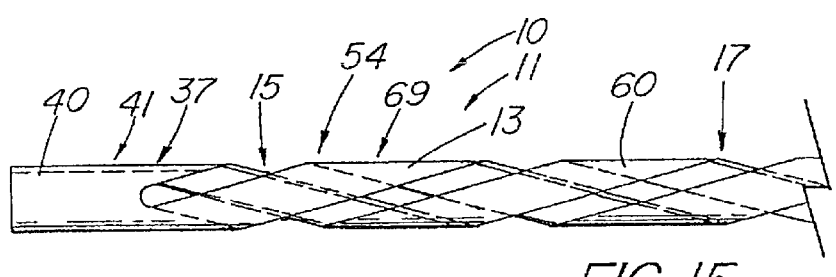
FIG. 15 depicts a side view of yet another alternative embodiment of the present invention in which the device includes a helical retrieval basket.
Figure 16:
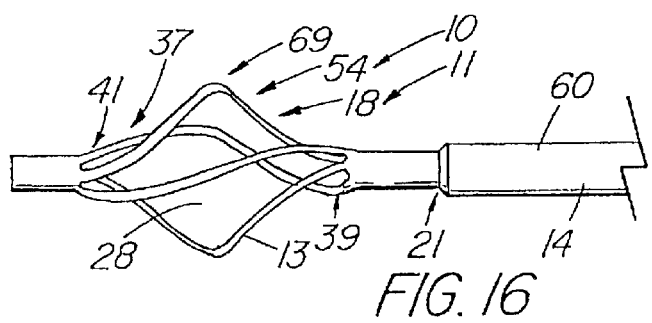
FIG. 16 depicts a side view of the device of FIG. 15 in an expanded state.

FIGS. 15–16 depict another preferred embodiment of the present invention in which the resilient grasping members 13 of retrieval device 10 are formed to produce a helical medical retrieval basket 10. FIG. 15 is a side view of an unexpanded four-wire helical basket 54 having spiral-shaped slots 15. The slots 15 can be formed in a similar manner to the embodiment of FIG. 1, the difference being that either the cutting means or the cannula 60 itself is rotated to produce slots 15 that spiral around the circumference of the cannula 60. This method of manufacture can also be adapted for use with solid wire. FIG. 16 depicts a side view of medical retrieval device of FIG. 15: as with the non-helical embodiments the resilient grasping members 13 are manually formed into the enlarged shape 18 where the grasping members 13 are in a relaxed, non-stressed state or condition.

Figure 18:
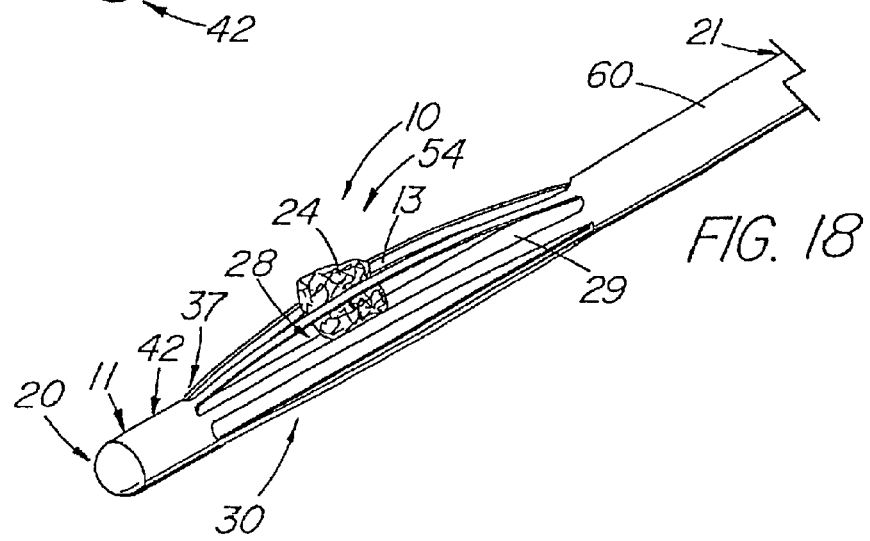
FIG. 18 depicts a pictorial view of the device of FIG. 17 in a closed position to grasp a calculus.

FIGS. 17–18 are pictorial views of an alternate embodiment of device 10 of FIG. 1 that includes an actuating member 29 rather than an external constraining mechanism, for opening and closing the basket to receive and grasp a calculus 24. In FIG. 17, the grasping members 13 are opened sufficiently to receive the calculus 24 into workspace 28. FIG. 18 depicts a pictorial view of retrieval device 10 of FIG. 16 in which the actuating member 29 has been fully advanced to urge the distal end 20 distally and close the resilient grasping members 13 firmly over the calculus 24. The distal end 42 of actuating member 29 is soldered or otherwise attached to the distal end 20 of device 10. While the unexpanded device is contained within an endoscope or introducer sheath, the actuating member 29 is in its fully advanced position. When the grasping members 13 have been exposed, the basket 54 is manipulated into the open or enlarged shape 18 by pulling back on the actuating member 29 which then can be locked into position. To close the basket, the actuating member 29 is fully advanced to the substantially closed position 30, ensnaring the calculus 24. The actuating member 29 may be locked into position at the proximal end 38 of the device by a locking hub or other well-known means to prevent accidental release of the calculus 24 while it is being withdrawn from the body.

While the actuating member does somewhat restrict the size of the workspace volume 28 available to receive a calculus, it eliminates the outer sheath, thereby allowing the device to occupy a smaller lumen or reach a more restricted space than would a coaxial device having the same diameter retrieval basket 54. The small-diameter actuating member may be used to still permit space within the lumen for additional instrumentation, or a second lumen could be reserved in the elongated member 11 for that purpose. It is important that the actuating member 29 must be of sufficient stiffness during advancement to force closure of the resilient grasping members without significant lateral flexure of the rod. Because the position of the actuating member 29 relative to the cannula 60 controls whether the basket is open or closed, the resilient grasping members 13 could be in the relaxed, non-stressed state while either in the enlarged shape, as with the other embodiments, or in the compact shape. In the case of the latter, withdrawing the actuating member 29 relative the cannula 60 opens the basket into the enlarged shape 18, while advancing actuating member will return the resilient grasping members 13 to the relaxed compact shape 17.

FIGS. 19–21 depict other preferred embodiments of retrieval device 10 of the present invention whereby the continuum of a first material 40 that comprises the resilient grasping members 13 can include a plurality of reinforcement wires 31 that are interconnected by another material 66 in the distal portion 37 of the elongated member 11 proximal to the grasping members 13. In the illustrative embodiments, the retrieval device 10 comprises a plastic tube 32 having flat resilient metal or plastic reinforcement wires 31 encased within the walls 16. By removing a portion of the plastic tube 32 in the distal portion 37 of the elongated member 11, the exposed reinforcement wires 31 function as resilient grasping members 13 after they are formed into the enlarged shape 18.

FIG. 19 depicts a retrieval basket 10 in which the resilient grasping members 13 are flat reinforcement wires 31 having a helical braid pattern 33 while encased in plastic tube 32. The resilient grasping members 13 can be redirected or straightened as they exit distal end 56 of the plastic tubing 32, or follow the natural contour of helical braid 33. It is possible to have fewer resilient grasping members 13 than exposed reinforcement wires 31 by truncating some of wires at the tube distal end 56 where they exit the tubing 32. In an example of a reinforced tube with eight braided wires, all helical wires of one direction (e.g., spirally clockwise) can be truncated, leaving four exposed wires spiraling the other direction for which to form a four-member helical basket. The distal ends 41 can be joined with a fastener 57 such as an end cap 34 or other well-known means. Another alternative of making a retrieval basket 54 is to leave a portion of the original plastic tube 32 at the distal end similar to distal cylinder 55 in FIG. 1 to interconnect the distal ends 41 of the resilient grasping members 13.

FIG. 20 depicts another preferred embodiment of the present invention whereby the reinforcement wires 31 are aligned with longitudinal axis 43 of the elongated member 11, rather than being helically wound. This type of basket would not normally require redirection or truncation of wires as they exit the distal end of the plastic tube 32.

FIG. 21 depicts an embodiment of the devices of FIGS. 18 and 19 in which the unsecured resilient grasper elements comprise grasper forceps 23. The distal ends 41 of the resilient grasping members 13 can be deformed inward to facilitate capture and retention of a target object.

FIGS. 22 and 23 depict an alternate embodiment of the device 10 of FIG. 1 wherein the distal portion 37 and the proximal portion 21 of the elongated member 11 are formed as separate members which are connected at a junction 59.

Referring to FIGS. 24 and 25, the junction 59 between the distal portion 37 and the shaft 63 holds the first passage 12 (of the distal portion 37) and the second passage 64 (of the shaft 63), in concentric alignment along longitudinal axis 43. The concentric alignment of the first and second passages 12, 64 forms a continuous lumen 65 from the proximal end of the shaft 63 through the entire device 10 and extending into the grasping area 28 adjacent to the grasping members 13. The shaft 63 is a flat wire braided tube comprising a hollow, braided, flat wire conduit 71 defining a bore 79, and that has been impregnated with a lubricious material such as polyimide as manufactured by HV Technologies, Trenton, Ga. The shaft 63 is held to the elongated cylindrical member 11 by epoxy 66 such as LOCTITE 4014, manufactured by Loctite Corp. a division of Henkel, Rocky Hill, Conn.

Referring to FIG. 25, the polyimide impregnates the flat wire braid 71 to form an inner sheath 70 and an outer sheath 72. The inner sheath 70 is adjacent to and defines the second passage 64. The flat wire metal braid 71 is preferably made from metallic wires such as flat stainless steel wires braided into a conduit to give good strength and flexibility. The conduit-shaped braid 71 surrounds the second passage 64. When the braided wires 71 are placed in tension, the conduit is constricted, so that axial forces which would otherwise tend to separate the shaft 63 from the distal portion 37 tend also to increase the constriction of the braid 71 on the distal portion 37.

Continuing to refer to FIG. 25, the distal portion 37 is machined to form a shoulder 81 and a stepped portion 78 of reduced outside diameter 74 adjacent the proximal end of the distal portion 37. The shaft 63 may also be machined to remove a portion of the inner sheath 70 adjacent its distal end to form an area of increased inner diameter 75 along bore 79 and exposing the flat wire metal braid 71 to the second passage 64.

Continuing to refer to FIGS. 24 and 25, to form the junction 59, the proximal end of the distal portion 37 is inserted into the distal end of the shaft 63. It should be understood, the reduced outside diameter 74 of the distal portion 37 and the inside diameter 75 of the shaft 63 are approximately equal to each other. The braid 71 of the shaft 63 surrounds and is joined to the stepped portion 78 of the distal portion 37. Adhesive such as the epoxy 73 forms a strong bond to prevent the two pieces 37, 63 from pulling apart. When tensioned, the braid 71 will grasp the distal portion 37 by constriction on the stepped portion 78. Referring also to FIG. 23, the coaxial relationship between the first lumen 12 and the second lumen 64 to form the continuous lumen 65 and the reduction to the outside diameter of the distal portion 37 at the stepped portion 78, allows a concentric fit of the distal portion 37 into the shaft 63 without causing the outside diameter 76 of the elongated member 11 to be increased substantially at the junction 59.

In addition, the diameter of the central lumen 65 is not affected by the junction 59, thereby forming a device 10 that maintains a minimal outside diameter 76 and a maximal inner diameter 77. In the preferred embodiment, the outside diameter 76 is approximately 3 Fr (1 mm) and the inner diameter 77 is capable of accepting a fiber optic cable 25 of at least 0.025 mm with cladding of up to 0.0365 mm or more with a minimal cladding referred to in the industry as "slim line cladding".

Continuing to refer to FIGS. 24 and 25, the shaft 63 further comprises an outer sheath 72 of a lubricious material such as polyimide. The outer sheath 72 covers and protects the metal braid 71 and reduces friction for moving the shaft 63 along the accessory channel 46 in the scope 44 (FIG. 8) or inside outer sheath 14 (FIGS. 7,8 and 14). It should be understood that the second passage 64 of the shaft 63 is critical to the use of laser, ultrasound or other accessory devices 25 for treating calculi 24 in the grasp of the holding members 11. The metal braid 71 allows the strength of stainless steel wire with a minimum wall thickness on the shaft 63 by the use of fine stainless steel wires in the braid 71.

Referring now to FIG. 26, an embodiment of the invention is shown wherein the device 10 utilizes a handle 86 as is known in the art of medical retrieval devices. The handle 86 has a sliding member 88 attached to the outer constraining member, or sheath 14. The sliding member 88 is slidably mounted in the handle body 92, so that a protrusion 90 from the sliding member 88 may be used to advance or retract the sliding member 88 with respect to handle body 92. A slot 93 is formed in the surface of the handle body 92 receives the protrusion 90 and limits the movement of the sliding member 88 with respect to the handle body 92. It should be understood that, by manipulation of the protrusion 90, the sheath 14 is moved with respect to the elongated member to cause the holding member to transform from its closed, or compact shape 17 (shown, for example, in FIG. 2) to its open, expanded position 18 (shown, for example, in FIG. 1).

Continuing to refer to FIG. 26, the shaft 63 extends through the sliding member 88 and is anchored to the handle body 92 at a receiving adapter 94. An orifice 95 (FIG. 27) is formed in the receiving adapter 94 along axis 43. The orifice is concentrically aligned with the continuous lumen 65 to allow, for example, a fiber optic cable 96, 25 attached to a laser power supply 98 to be inserted into the orifice and through the continuous lumen 65 to direct laser energy at a stone or calculi 24 (FIG. 8) captured by the resilient grasping members 13 for breaking up the stone or calculi 24, which may then be removed from the patient. Alternatively, the continuous lumen 65 in communication with the orifice 95 may be used to guide a lithotripsy wire 99, 25 from an ultrasound power supply 100 to the stone or calculus 24.

The retrieval device 10 of the present invention preferably comprises medical grade materials which can be sterilized by conventional procedures prior to use. Conveniently, the retrieval device 10 can be made of relatively inexpensive synthetic and metallic materials, so that the device 10 can be disposed of after a single use, rather than being resterilized and reused. Such reuse, however, is also contemplated within the scope of the invention. It should be understood that, although passages 12 and 64 are described as aligned along axis 43, forming the continuous central lumen 65, the device is intended to be used wherein the lumen 65 does not extend along a straight line. Coaxial alignment of the passages 12 and 64 is necessarily maintained as the device 10 is manipulated. The strength and flexibility of the shaft 63 attached to the distal portion 37 is therefore an important feature of the present invention.

Of course, these and the other details of construction can be changed to adapt the retrieval device 10 of the present invention to the particular surgical technique to be performed.

It should be clear from the foregoing disclosure that the retrieval device 10 of the present invention is particularly advantageous over prior devices in a variety of ways. Most important, the present invention is particularly advantageous over the prior art in that the device (and in particular, its outer sheath) can have an overall outside diameter significantly smaller than the outside diameter of existing retrieval or extraction devices. Indeed, the retrieval device of the present invention can have an outside diameter as small as 1 Fr (0.33 mm). The retrieval device of the present invention is expected to allow the capture, removal, extraction and/or retrieval of stones, calculi, concretions, foreign bodies and the like from locations in the body much deeper than can be achieved with existing devices. The basket, grasper or other engagement means formed from the wedge-cross-sectional-shaped wires enjoys the good resistance to twisting and bending, despite this small diameter, and as noted in the preferred embodiment of the invention is capable of being formed and maintained in a helical shape, just like round wires. The smaller overall diameters enjoyed by the present invention should also reduce the risk of patient trauma during use.

As noted above, the retrieval device of the present invention is expected to find use in a wide variety of procedures, including urological procedures, biliary procedures, vascular procedures and procedures for the retrieval of foreign objects from a variety of body cavities. Moreover, retrieval devices of the present invention formed from a cannula or tube, offer the ability to introduce a laser fiber or other treatment device, or feed the retrieval device over a guide wire to facilitate placement within the body.

The details of the construction or composition of the various elements of the retrieval device 10 not otherwise disclosed are not believed to be critical to the achievement of the advantages of the present invention, so long as the elements possess the strength or flexibility needed for them to perform as disclosed. The selection of any such details of construction is believed to be well within the ability of one of even rudimentary skills in this area, in view of the present disclosure.

What is claimed is:

1. A medical retrieval device comprising:
   an elongated cylindrical member having a passage extending therein and having metallic proximal and distal portions, and a retrieving portion defined in the distal portion, wherein the distal portion is formed from a metal and includes a shoulder and stepped portion of reduced outside diameter at a proximal end of the distal portion;
   said proximal and distal portions formed as separate pieces and connected at a junction; and
   whereby the elongated cylindrical member has an area of substantially constant inner and outer diameters extending at least from a portion of the proximal portion closely adjacent to the junction through the junction and to a portion of the distal portion closely adjacent to the junction.

2. The medical device of claim 1 wherein the retrieving portion includes a plurality of resilient grasping members.

3. The medical device of claim 2 wherein the resilient grasping members are manipulable between a compact shape and an enlarged shape, wherein the resilient grasping members of the enlarged shape are in a relaxed condition.

4. The medical device of claim 3, further comprising an external constraining mechanism to constrain the distal portion of the elongated cylindrical member into the compact shape, the external constraining mechanism being longitudinally slidable about the elongated cylindrical member to alternately deploy the resilient grasping members to the enlarged shape, or recompress the resilient grasping members having the enlarged shape into one of the compact shape or a substantially closed position for capture or capture and retrieval of an object from within a patient.

5. The medical device of claim 2 wherein the resilient grasping members, each having a distal end and a proximal end, are conjoined about the distal ends thereof.

6. The medical device of claim 5 wherein the distal portion comprises a proximal closed cylinder and a distal closed cylinder and the resilient grasping members extend between the proximal closed cylinder and the distal closed cylinder.

7. A medical retrieval device comprising:
an elongated cylindrical member having a passage extending therein and having a proximal portion including a braided sleeve and a distal portion, a retrieving portion defined in the distal portion, said proximal and distal portions formed as separate pieces and connected at a junction, the distal portion formed from a continuum of metal; and
whereby the elongated cylindrical member has an area of substantially constant inner and outer diameters extending at least from a portion of the proximal portion closely adjacent to the junction through the junction and to a portion of the distal portion closely adjacent to the junction, wherein the proximal and distal portions are joined at the junction by a technique selected from the group consisting of welding, brazing, soldering and crimping.

8. The medical device of claim 7, wherein at least one of the proximal and distal portions comprises stainless steel or a superelastic alloy.

9. The medical device of claim 7, wherein the retrieving portion includes a plural of resilient grasping members, and wherein the resilient grasping members have been heat treated for an enlarged shape in which bending stresses of the resilient members are removed.

10. The medical device of claim 9, wherein the retrieving portion comprises a proximal closed cylinder and a distal closed cylinder and the resilient grasping members extend between the proximal and distal closed cylinders.

11. The medical device of claim 9, further comprising an external constraining mechanism to constrain the distal portion of the elongated cylindrical member into the compact shape, the external constraining mechanism being longitudinally slidable about the elongated cylindrical member to alternately deploy the resilient grasping members to the enlarged shape, or recompress the resilient grasping members having the enlarged shape into one of the compact shape or a substantially closed position for capture or capture and retrieval of an object from within a patient.

* * * * *